United States Patent [19]

Stutz, Jr. et al.

[11] Patent Number: 5,873,899

[45] Date of Patent: Feb. 23, 1999

[54] IMPLANTABLE MEDICAL DEVICE HAVING COMPLIANT SUPPORT FOR INTERNAL COMPONENTS

[75] Inventors: William H. Stutz, Jr., Los Angles; Clyde K. Nason, Valencia, both of Calif.

[73] Assignee: Pacesetter Inc., Sylmar, Calif.

[21] Appl. No.: 586,527

[22] Filed: Jan. 16, 1996

[51] Int. Cl.$^6$ .................................................. A61N 1/375
[52] U.S. Cl. ............................................................ 607/36
[58] Field of Search .................................. 607/2, 36, 55, 607/57; 361/736

[56] References Cited

U.S. PATENT DOCUMENTS

| | | | |
|---|---|---|---|
| 3,943,937 | 3/1976 | King et al. | 607/36 |
| 4,041,956 | 8/1977 | Purdy et al. | 607/36 |
| 4,243,042 | 1/1981 | Ware | 607/36 |
| 4,314,562 | 2/1982 | Ware | 607/36 |
| 5,431,695 | 7/1995 | Wiklund et al. | 607/36 |
| 5,456,698 | 10/1995 | Byland et al. | 607/36 |

*Primary Examiner*—William E. Kamm
*Assistant Examiner*—Carl H. Layno

[57] ABSTRACT

An implantable medical device, in the form of a cardiac defibrillator, has a support structure of molded thermoplastic foam surrounding the components of the device within a case to provide the components with shock and vibration resistance. The thermoplastic foam is produced by a process using dry nitrogen blowing, so as to be chemically inert. This prevents harmful outgassing of chemicals from the foam. The thermoplastic foam is a low density, crosslinked foam of polyethylene or polypropylene composition. The support structure includes an opposite pair of supports molded from the thermoplastic foam, so as to have facing portions configured to the irregular shape and size of the components. Each support is made by preheating an opposing pair of dies and a thermoplastic foam element, compressing the preheated foam element between the opposing dies, and heating for a predetermined time at a predetermined temperature, cooling the dies, and then removing the formed support from the dies.

9 Claims, 2 Drawing Sheets

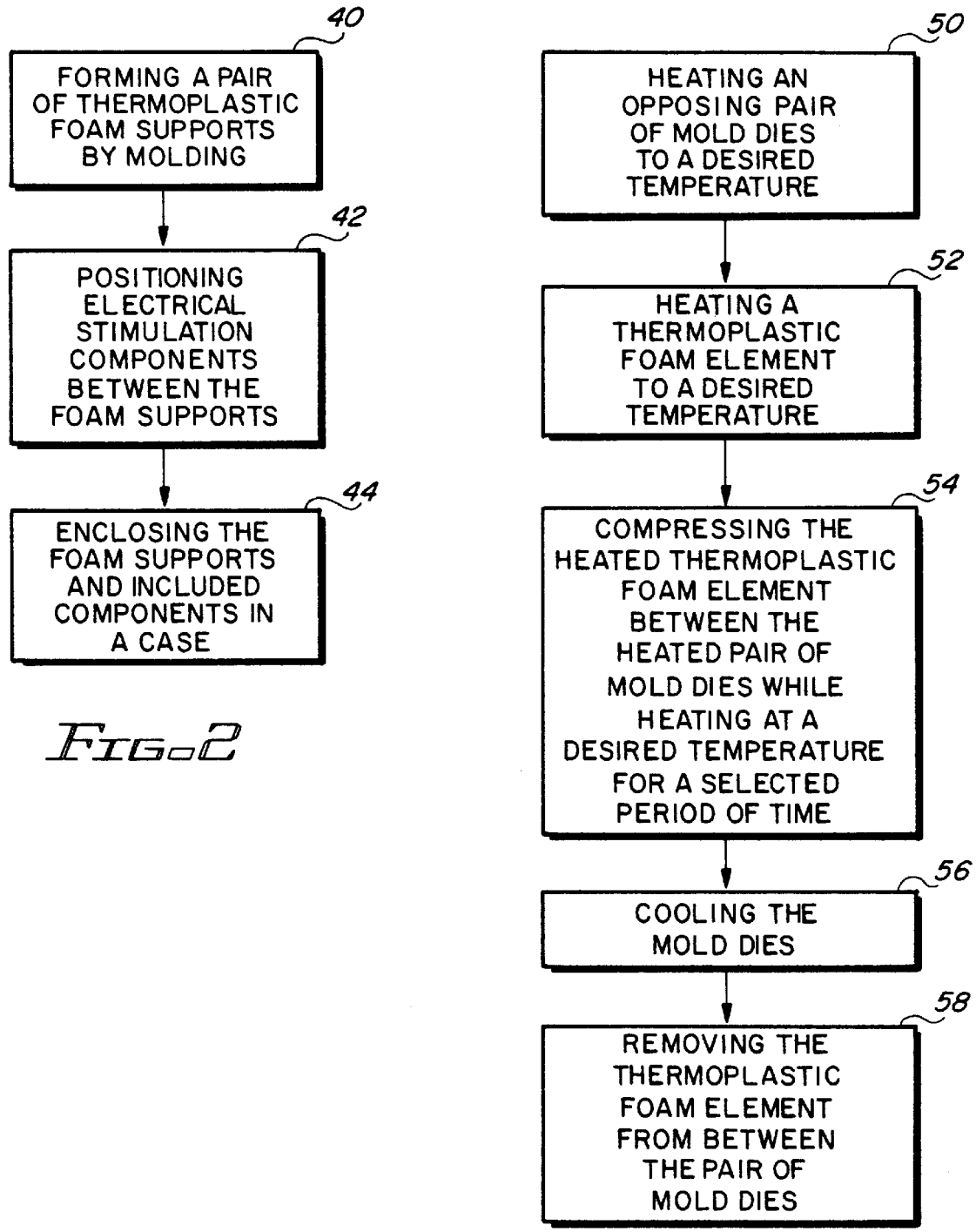

IMPLANTABLE MEDICAL DEVICE HAVING COMPLIANT SUPPORT FOR INTERNAL COMPONENTS

FIELD OF THE INVENTION

The present invention relates generally to implantable medical devices, such as cardiac defibrillators and cardiac pacemakers, and more particularly, to compliant supports for packaging the internal electronic components of the device within a case for the device.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, a cardiac defibrillator. The appended claims are not intended to be limited, however, to any specific example or embodiment described herein.

Implantable medical devices, such as cardiac defibrillators and cardiac pacemakers, are implanted within the body of a person so that battery powered electronic components therein are electrically interconnected with the body. Defibrillating or pacing pulses emitted by the components are applied to stimulate selected body tissue. At the same time, the condition of the stimulating activity within the body can be fed back to the electronic components for sensing.

Typically, an implantable medical device includes thin, oval- or rectangular-shaped can, or case, which is surgically implanted beneath the skin in the chest region or the abdomen. The electronic components, together with batteries for powering the same, are mounted on the inside of the can, and are coupled by a feedthrough assembly to a connector assembly on the outside of the case. One or more leads received by the connector assembly electrically couple the electronic components to transvenous connection of the lead within the person.

In implantable medical devices of this type, the electronic components are internally packaged within the case by a support structure which serves not only to mount the components but to provide some resistance to shock and vibration as well. The support structure may be made of resilient material, such as silicon rubber, which electrically insulates the components from the case, as well as providing some shock and vibration resistance. Such resistance, however, is limited in view of the relative hardness of the material and the typical gasket-like configuration thereof which is lacking in dimensional detail so as to provide little conformance to the components. Still other support structures have been made of rigid thermoplastic material, such as liquid crystal polymer, which, among other things, has proven capable of withstanding the temperatures of almost 600° F. present during welding of the case. While such rigid thermoplastic materials may be formed so as to provide pockets and otherwise more closely conform to the shape of the components, they have been found to provide relatively little in the way of resistance to shock and vibration. Additionally, these precisely formed rigid pockets do not conform to the size tolerance variations of the components. One lot of components may be loose in the pockets and rattle, while those from the next lot may be excessively tight.

A major problem with support structures heretofore used in implantable medical devices is the tendency of the material to outgas chemical products after the device is assembled and placed in use. Because the materials of the support structure are typically made in the presence of non-inert chemicals, outgassing of such chemicals after the device is completed and placed in use, interferes with and eventually contaminates the electronic components.

In addition to the use of resilient materials, such as silicon rubber and relatively rigid thermoplastic material in the formation of support structures for implantable medical devices, it is known in the art to encapsulate electronic components by injecting foam-like materials into a cavity in which the electronic components are placed. In the case of integrated circuit boards, for example, it is known to position the board or portions thereof within a cavity of a mold and to introduce foam so as to surround and encapsulate the board. Examples of these techniques are provided by U.S. Pat. No. 4,250,347 to Fierkens, issued Feb. 10, 1981; U.S. Pat. No. 5,254,501 to Tung, issued Oct. 9, 1993; and U.S. Pat. No. 5,018,003 to Yasunaga et al., issued May 21, 1991.

In spite of this prior work, however, the field of implantable medical devices has heretofore been without the benefit of a support structure having the necessary characteristics of being able to package the internal components in a conforming, shock and vibration resistant fashion, and with relative lightness in weight. In particular, chemical inertness has not been a characteristic of prior art support structures.

Consequently, it would be highly desirable to provide a support structure made of compliant material which avoids such undesirable outgassing effects in addition to providing superior shock and vibration resistance. The support structure should also be relatively light in weight, inasmuch as certain applications of the devices, particularly in the case of cardiac defibrillators, include relatively heavy batteries and other components which can add significantly to the weight of the device.

SUMMARY OF THE INVENTION

Briefly stated, implantable medical devices in accordance with the invention package the electronics, batteries, capacitors and other internal components within the enclosing case of the device using a support structure which conforms to the shape and size variations of the components and is made of material providing the requisite shock and vibration resistance, as well as relative lightness in weight. In addition, and of equal importance, is the fact that the support structure is made from chemically inert material which does not outgas chemicals which are harmful to the internal components.

In a preferred embodiment of an implantable medical device according to the invention, the internal components of a cardiac defibrillator are disposed between opposite supports of molded foam material. The supports are molded with the facing surfaces thereof configured so as to conform to the particular shape of the components, as well as allow for size tolerance variations of same. The opposite supports and included components are placed within the opposite halves of a case, with the case halves then being joined together in sealed fashion. The supports are made of foamed thermoplastic material and may be a low density, crosslinked foam of either polyethylene or polypropylene composition. The foam is made by a dry nitrogen blowing process to render it chemically inert.

In a preferred method of making an implantable medical device according to the invention, a pair of thermoplastic foam supports are formed by molding. The electrical components, including the electronic circuits, capacitors and the batteries therefor are then positioned between the foam supports, before enclosing the foam supports and the included components within an outer case. To form each of the pair of thermoplastic foam supports, an opposing pair of mold dies is heated to a desired temperature. At the same time, a thermoplastic foam element is heated to a desired temperature. The heated thermoplastic foam element is then compressed between the heated pair of mold dies, while heating to a desired temperature and for a selected period of time. The mold dies are then cooled, after which the thermoplastic foam element is then removed from the pair of mold dies.

BRIEF DESCRIPTION OF THE DRAWINGS

Further objects, advantages and features of the invention will become apparent from the detailed description of the preferred embodiment when read in conjunction with the accompanying drawings, in which:

FIG. 2 is a block diagram of the successive steps in a preferred method of making the device of FIG. 1; and FIG. 3 is a block diagram of the successive steps in a preferred method of making the foam supports in the device of FIG. 1.

DESCRIPTION OF THE PREFERRED EMBODIMENT

Figure 1:
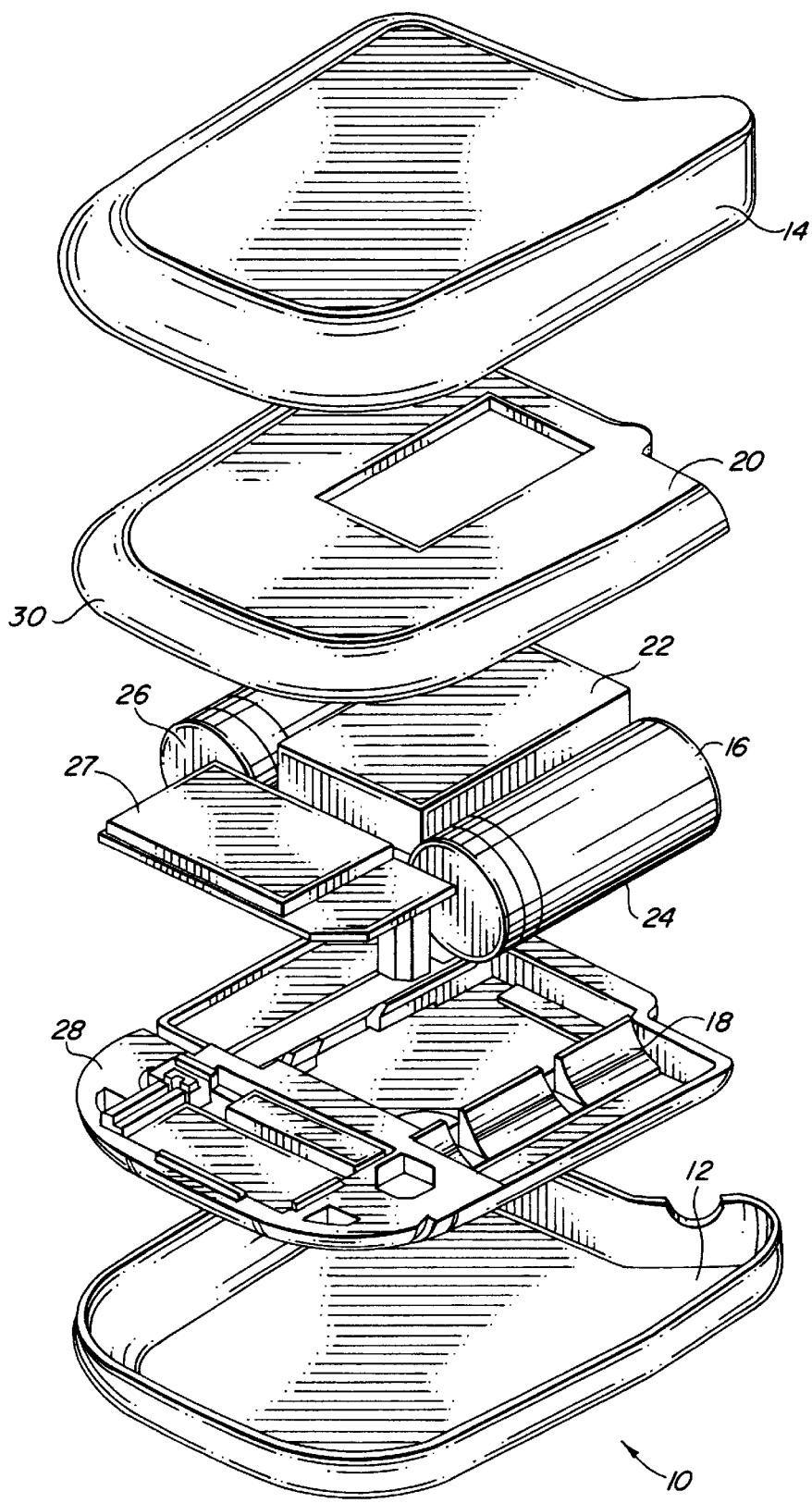
FIG. 1 is an exploded perspective view of an implantable medical device in accordance with the invention.

FIG. 1 is an exploded perspective view of an implantable medical device 10 according to the invention. The device 10 of FIG. 1 includes an opposing pair of case halves 12 and 14 which may be joined together in sealed fashion such as by welding to form an enclosed case or can for the device 10. The device 10 also includes components 16 which are packaged within the case halves 12 and 14 by an opposing pair of foam supports 18 and 20 in accordance with the invention. The components 16 are conventional in nature and include electronic circuits, as well as batteries and capacitors for powering such circuits. In the example of FIG. 1, the components 16 include two piggybacked batteries 22 having a pair of capacitors 24 and 26 mounted on opposite sides thereof. A hybrid microelectronic module 27 and a feedthrough assembly of conventional configuration (not shown) may be used to couple the components 16 to leads on the outside of the assembled case halves 12 and 14.

The foam supports 18 and 20 are molded so as to have facing surfaces 28 and 30 thereof which conform to the irregular external shape of the components 16. In this manner, the foam supports 18 and 20 engage opposite sides of the components 16 in conforming, form-fitting fashion, regardless of the size of the components. This enables the foam supports 18 and 20 to package the components 16 within the case halves 12 and 14 in superior fashion. At the same time, the thermoplastic foam used to form the supports 18 and 20 provides the requisite resistance to shock and vibration, while at the same time being sufficiently light in weight as well as chemically inert.

In accordance with the invention, the foam supports 18 and 20 are made of thermoplastic foam which has the desired properties. Preferably, the foam comprises a low density, crosslinked foam of either polyethylene or polypropylene composition. Most importantly, the foam must be chemically inert to prevent harmful outgassing therefrom.

A thermoplastic foam which is suitable for use in forming the foam supports 18 and 20 is sold under the trademark "Plastazote" by Zotefoams Ltd. of Surrey, England. Plastazote is a low density, crosslinked foam formed using a dry nitrogen blowing process so as to render the foam chemically inert. Plastazote LD60 is a medium density polyethylene form of the foam which has been successfully used in forming foam supports according to the invention. Of course, it will occur to those skilled in the art that other thermoplastic foams may be suitable for use in accordance with the invention, so long as they have the requisite properties as described herein.

A preferred method of making the device 10 of FIG. 1 is illustrated by the successive steps of FIG. 2. In a first such step 40, a pair of thermoplastic foam supports, such as the foam supports 18 and 20 of FIG. 1, are formed such as by molding. In a following step 42, electrical stimulation components, such as the components 16 of FIG. 1, are positioned between the foam supports formed in the first step 40. In a third step 44, the foam supports and the included components are enclosed within a case, such as the case formed by the case halves 12 and 14 of FIG. 1. Typically, the case halves 12 and 14 are made of strong and lightweight material, such as titanium, and are joined together in sealed fashion, such as by welding.

The successive steps of a preferred method of making the foam supports 18 and 20 are set forth in FIG. 3. In a first step 50, an opposing pair of male and female dies are preheated to a desired temperature. At the same time, and in a second step 52, a thermoplastic foam element is heated to a desired temperature. Where Plastazote foam is used, such foam is manufactured in sheets of approximately 6 inches thick. Such sheets are sliced into sheets approximately one-half inch thick, and the one-half inch thick sheets are cut into appropriate sizes for compression molding using the opposing preheated dies. The one-half inch sheet stock is preheated to a temperature of approximately 300° F. before placement between the preheated mold dies.

In a third step 54 shown in FIG. 3, the preheated thermoplastic foam element is compressed between the opposing pair of mold dies at an appropriate temperature and for an appropriate period of time. Typically, the mold dies and included foam element are heated to approximately 220° F. for one-half to one minute. Following that, and in a fourth step 56, the mold dies are cooled, such as by use of water cooling, before removing the thermoplastic foam element. This prevents expansion of the thermoplastic foam element following removal from the mold dies. When the mold dies and the thermoplastic foam element have been cooled to a sufficient extent, then in a fifth step 58 the thermoplastic foam element is removed from the mold dies to provide the foam support.

While the invention has been described in connection with a preferred embodiment, it will be understood that it is not intended to limit the invention thereto, but that it is intended to cover all modifications and alternative constructions falling within the spirit and scope of the invention as expressed in the appended claims.

What is claimed is:

1. An implantable medical device for implantation in a human body, comprising the combination of:

components for electrical interconnection with a human body in which the device is to be implanted;

a pair of supports disposed on opposite sides of and receiving the components therebetween, each of the supports being made of foamed thermoplastic material; and a case surrounding and receiving the pair of supports and the components therein.

2. An implantable medical device, in accordance with claim 1, wherein the foamed thermoplastic material comprises dry nitrogen blown, chemically inert foam.

3. An implantable medical device, in accordance with claim 1, wherein the foamed thermoplastic material consists of chemically inert, crosslinked, low density polyethylene foam.

4. An implantable medical device, in accordance with claim 1, wherein the components are of irregular shape and size, and each of the pair of supports has a surface thereof molded to conformingly receive the components of irregular shape and size.

5. An implantable medical device for implantation in a human body, comprising the combination of:

componentsfor electrical interconnection with a human body in which the device is to be implanted;

an enclosed case containing the components; and a support structure disposed within the case and receiving the components therein, the support structure surrounding the components within the case to provide shock and vibration resistance and consisting of at least one element of molded foam which is chemically inert;

wherein the molded foam comprises dry nitrogen blown foam from the group consisting of polyethylene foam and polypropylene foam.

6. A method of making an implantable medical device, comprising the steps of:

molding a support structure of thermoplastic foam;

positioning electrical stimulation components within the support structure; and positioning the support structure and the included components within an enclosed case to form the device;

wherein the step of molding a support structure of thermoplastic foam comprises molding an opposite pair of supports with facing surfaces configured to conform to adjacent portions of the components when the pair of supports is joined together to surround and receive the components therein.

7. A method, in accordance with claim 6, wherein each of the opposite pair of supports is made by compression molding thermoplastic foam elements.

8. A method, in accordance with claim 7, wherein the making of each of the opposite pair of supports by compression molding thermoplastic foam elements comprises the steps of:

heating an opposing pair of mold dies;

heating a thermoplastic foam element;

compressing the heated thermoplastic foam element between the heated pair of mold dies and heating for a selected time;

cooling the mold dies; and removing the thermoplastic foam element from between the pair of mold dies.

9. A method, in accordance with claim 8, wherein the thermoplastic foam elements consist of dry nitrogen blown, chemically inert foam.

* * * * *